(12) United States Patent
Goff

(10) Patent No.: US 8,220,307 B2
(45) Date of Patent: Jul. 17, 2012

(54) RADIAL COMPRESSION MECHANISM WITH OPTIMUM DIE-TO-DIE GAP

(76) Inventor: Ed Goff, Phoenix, AZ (US)

(*) Notice: Subject to any disclaimer, the term of this patent is extended or adjusted under 35 U.S.C. 154(b) by 0 days.

(21) Appl. No.: 13/111,176

(22) Filed: May 19, 2011

(65) Prior Publication Data
US 2011/0214476 A1 Sep. 8, 2011

Related U.S. Application Data

(62) Division of application No. 11/842,882, filed on Aug. 21, 2007, now Pat. No. 7,963,142.

(51) Int. Cl.
*B21D 41/04* (2006.01)
*B21D 39/04* (2006.01)
(52) U.S. Cl. .............. 72/402; 29/282; 29/283.5
(58) Field of Classification Search .......... 72/402, 72/416, 452.1, 452.2, 452.4, 468, 482.92; 29/282, 283.5, 516
See application file for complete search history.

(56) References Cited

U.S. PATENT DOCUMENTS

| 3,203,078 | A  | * | 8/1965  | Ustin ............................ 29/862 |
| 7,152,452 | B2 | * | 12/2006 | Kokish .......................... 72/402 |
| 7,284,401 | B2 | * | 10/2007 | Larson et al. .................. 72/44 |
| 7,415,861 | B2 | * | 8/2008  | Sokel ............................ 72/402 |
| 2005/0229670 | A1 | * | 10/2005 | Perreault ...................... 72/402 |

* cited by examiner

*Primary Examiner* — Debra Sullivan
(74) *Attorney, Agent, or Firm* — Parsons & Goltry; Robert A. Parsons; Michael W. Goltry

(57) ABSTRACT

Radial compression mechanism includes a plurality of dies each having an elongated arcuate body with an outer end pivotally attached to a hinge plate and an inner working tip. The dies are mounted on the hinge plate in an inwardly spiraling orientation with the outer ends positioned in a circle and the working tips cooperating to define a central product-receiving cylindrically-shaped cavity. The product-receiving cavity is transitional between an open and a closed orientation. The working tip of each die has a sliding surface and a working surface with the sliding surface positioned in parallel juxtaposition to the working surface of an adjacent die and a constant width gap therebetween. Driving mechanism is coupled to rotatably drive all of the dies in unison to transition between open and closed orientations. The width of the gap remains constant during transition and between the open and closed orientations.

3 Claims, 16 Drawing Sheets

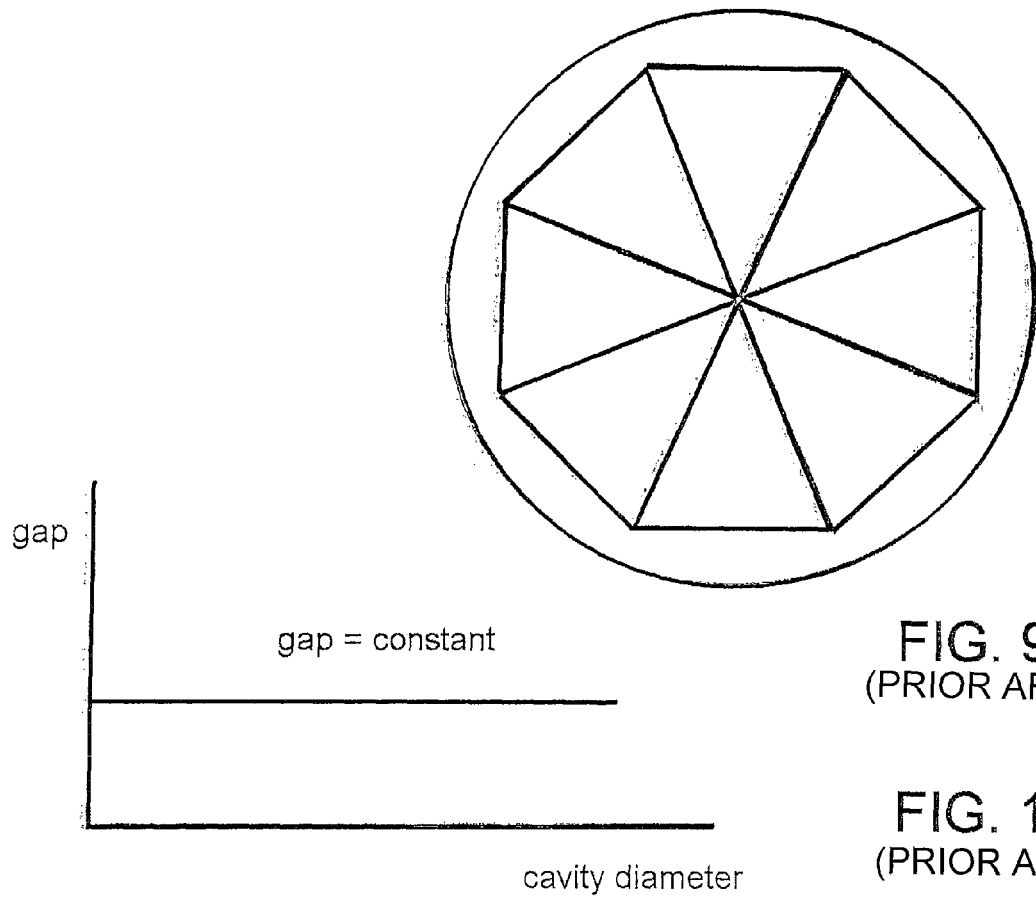
FIG. 9 (PRIOR ART)
FIG. 10 (PRIOR ART)
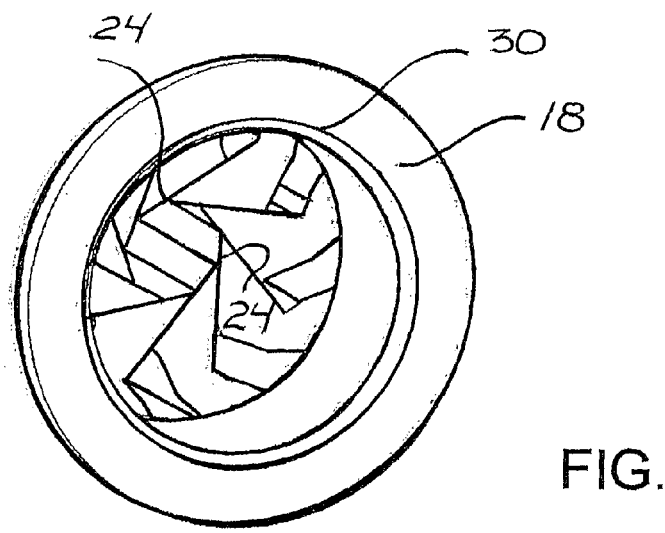
FIG. 12

RADIAL COMPRESSION MECHANISM WITH OPTIMUM DIE-TO-DIE GAP

CROSS-REFERENCE TO REALTED APPLICATIONS

The application is a divisional application of U.S. application Ser. No. 11/842,882, filed 21 Aug. 2007, which is now U.S. Pat. No. 7,963,142.

FIELD OF THE INVENTION

This invention generally relates to radial compression mechanisms and more specifically to mechanisms for compressing devices such as stents, catheters, balloons, and the like.

BACKGROUND OF THE INVENTION

In the manufacture and testing of medical devices, mechanisms are used to radially compress cylindrical devices such as stents, balloons, and catheters. For example, installation of a stent onto a catheter balloon is typically done by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In an example of medical device testing, a stent is radially compressed while the required force is measured, in order to measure the stent's functional relationship between diameter and radial force.

A first type of prior art device includes a radial compression mechanism wherein several similar wedge-shaped dies with planar surfaces are arranged to form an approximately cylindrical central cavity, the wedges being hinged and driven in unison to change the diameter of the cavity. A mechanism of this type is illustrated in FIGS. 1 through 5. Examples of this mechanism are the Crimpfox tool sold by Phoenix Contact GmbH 7 Co. KG (CRIMPFOX UD 6-6, Part Number 1206366), and the "segmental compression mechanism" marketed by Machine Solutions Incorporated, and described in U.S. Pat. No. 6,968,607. In this type of mechanism, the working surfaces of the dies have a wedge shape with two planar surfaces meeting at the tip. A shortcoming of this type of mechanism is that there exists a gap between adjacent wedges, the size of which varies with the diameter of the cavity in an undesirable way. Typically, the mechanism is specifically designed to provide a desired range of cavity diameters. At the lowest and highest diameters, the dies are tightly wedged against each other (zero gap). As the diameter is increased from the lowest, the gap increases until it reaches a maximum, then decreases until it becomes zero again at the highest diameter, as illustrated graphically in FIG. 5. The diameter range and gap (as a function of diameter) depend on the specific design of the mechanism, particularly the location of the hinge point of the dies and the diameter of the circle formed by all of the die hinge points in the mechanism. A larger diameter of the hinge point circle results in a smaller maximum gap for a given diameter range. The strict design tradeoffs for this type of mechanism results in a mechanism that must be large to provide a small maximum gap for a given diameter range, or a mechanism that must have a large gap to provide the same diameter range in a small size. Large gaps between the wedges are a disadvantage because they allow space for parts of the compressed device to go into. For example, the metal struts of a stent can move into the gap and be damaged.

A second type of prior art device includes a radial compression mechanism wherein several similar wedge-shaped dies with planar surfaces are arranged to form an approximately cylindrical central cavity, the wedges being attached to linear guides and driven in unison to change the diameter of the central cavity. A mechanism of this type is illustrated in FIGS. 6 through 10. Examples of this mechanism include the mechanism taught by Kokish in U.S. Pat. No. 6,651,478. or the mechanism marketed by Interface Associates Inc. (Model W8FH). In this type of mechanism, the working surfaces of the dies have a wedge shape with two planar surfaces meeting at the tip. The linear motion of the wedges in this mechanism provides a wedge-to-wedge gap that is constant, independent of the cavity diameter, and may be designed to be any desired size (see FIG. 10). A shortcoming of this mechanism is that it typically does not provide a sufficiently accurate positional relationship of the wedge-shaped working ends of the dies. Accurate positional relationship of the dies is important so that the central cavity remains approximately round and provides even compression around the circumference of the compressed device, and so that the largest die-to-die gaps aren't much larger than the average. Because each die is carried on its own linear guide, and all of the guides are attached to a plate or base, many parts and attachments may influence the accuracy (roundness) of the central cavity. Medical device manufacturing and testing often requires an accurately round cavity at diameters as small as 0.3 mm. which is typically not achieved by this type of mechanism.

It would be highly advantageous, therefore, to remedy the foregoing and other deficiencies inherent in the prior art.

Accordingly, it is an object of the present invention to provide a new and improved radial compression mechanism.

Another object of the invention is to provide a new and improved radial compression mechanism for compressing devices such as stents, catheters, balloons, and the like in the medical industry.

Another object of the invention is to provide a new and improved radial compression mechanism utilizing radially movable die that produce optimum die-to-die gaps.

SUMMARY OF THE INVENTION

Briefly, to achieve the desired objects of the present invention in accordance with a preferred embodiment thereof radial compression mechanism is provided that includes a plurality of dies each having an elongated arcuate body with an outer end pivotally attached to a hinge plate and an inner working tip. The dies are mounted on the hinge plate in an inwardly spiraling orientation with the outer ends positioned in a circle and the working tips cooperating to define a central product-receiving cylindrically-shaped cavity. The product-receiving cavity is transitional between an open and a closed orientation. The working tip of each die has a sliding surface and a working surface with the sliding surface positioned in parallel juxtaposition to the working surface of an adjacent die and a constant width gap therebetween. Driving mechanism is coupled to rotatably drive all of thes die in unison to transition between open and closed orientations. The width of the gap remains constant during transition and between the open and closed orientations.

The objects and other aspects of the invention are further achieved in a radial compression mechanism including a plurality of dies each including a generally wedge-shaped body having an outer end pivotally attached to a hinge plate and an inner working tip. The plurality of dies are mounted on the hinge plate in an inwardly directed orientation with the outer ends positioned in a circle and the working tips cooperating to define a central product-receiving cylindrically-shaped cavity having a transitional diameter coaxial with the circle. The diameter of the product-receiving cavity is transitional between an open and a closed orientation. Each die of the plurality of dies has a sliding surface and a working surface with a juncture of the sliding surface and the working surface defining the working tip. The sliding surface of each die of the plurality of dies is substantially concave and the working surface of each die of the plurality of dies is substantially convex. The concave sliding surface of each die is positioned in juxtaposition to the convex working surface of an adjacent die and the concave sliding surface of each die is formed to mate with the convex working surface of the adjacent die. A constant width gap is defined between the working tip of each die of the plurality of dies and the working surface of the adjacent die of the plurality of dies. Driving mechanism coupled to each die of the plurality of dies rotatably drives all of the dies of the plurality of dies in unison to transition between the open and closed orientations. The width of the gap remains constant in the open and closed orientations and during the transition between the open and closed orientations.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIGS. 6-9 illustrate a second type of prior art radial compression mechanism with linear movement of the die;

FIG. 10 illustrates graphically the relationship between the diameter of the central opening and die-to-die gaps for the embodiment of FIG. 6;

FIG. 12 is an enlarged view in perspective of the receiving opening in the mechanism of FIG. 1;

DETAILED DESCRIPTION OF A PREFERRED EMBODIMENT

Figure 1:
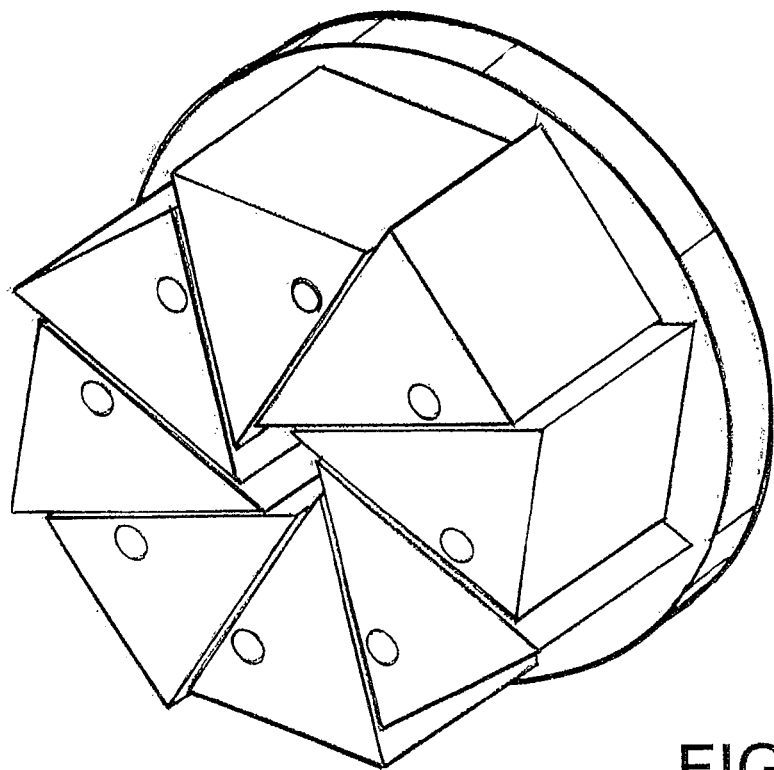
FIGS. 1-4 illustrate a first type of prior art radial compression mechanism.
Figure 2:
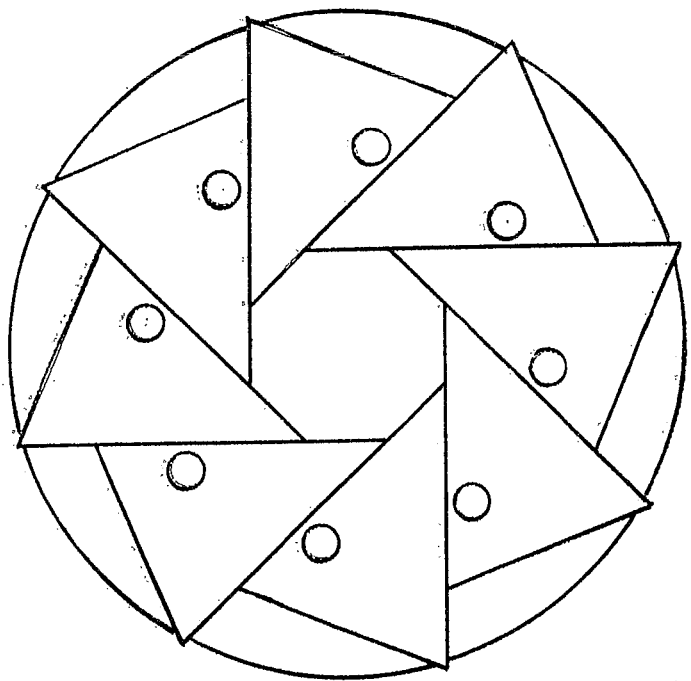
Figure 3:
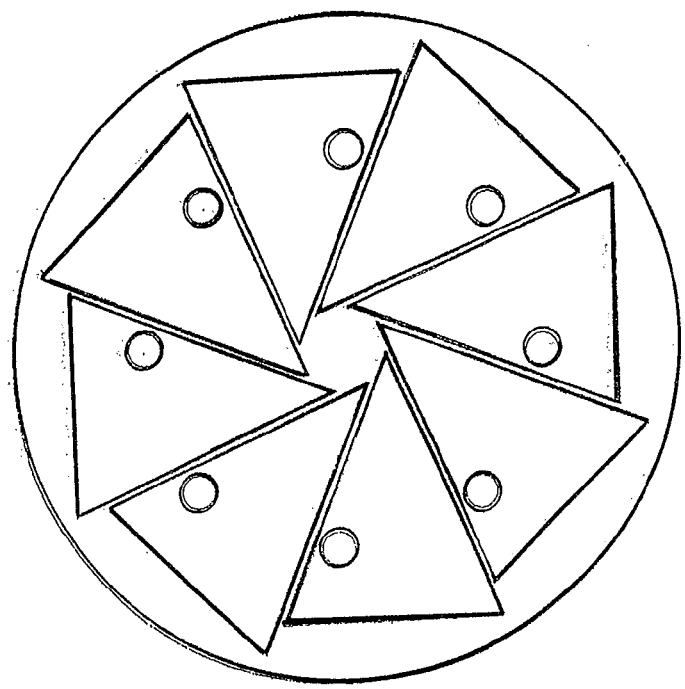
Figure 4:
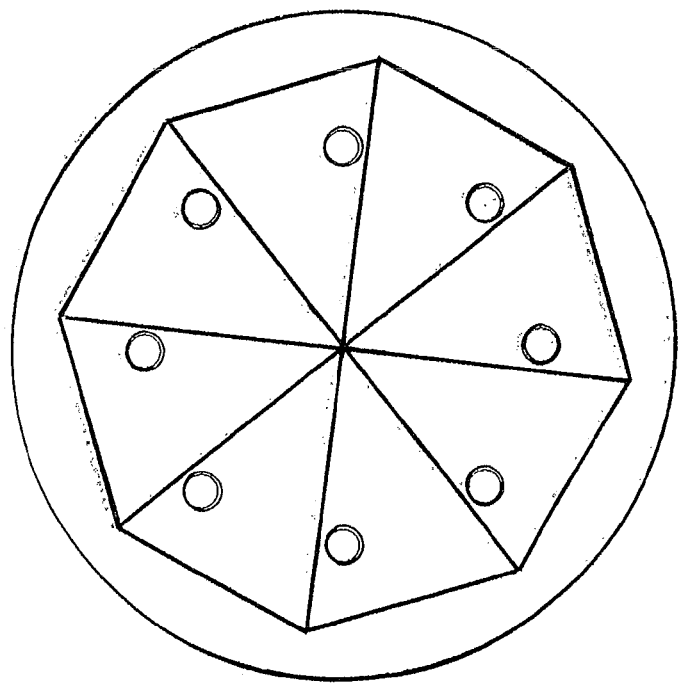
Figure 5:
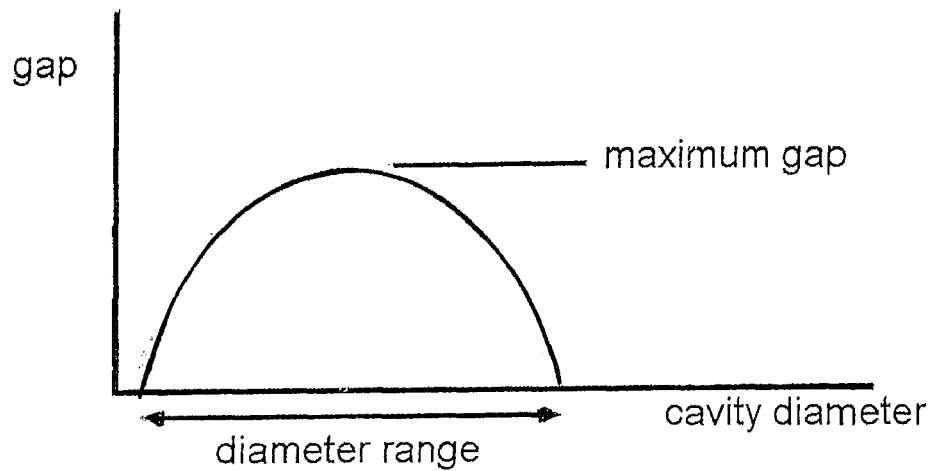
FIG. 5 illustrates graphically the relationship between the diameter of the central opening and die-to-die gaps for the embodiment of FIG. 1.
Figure 6:
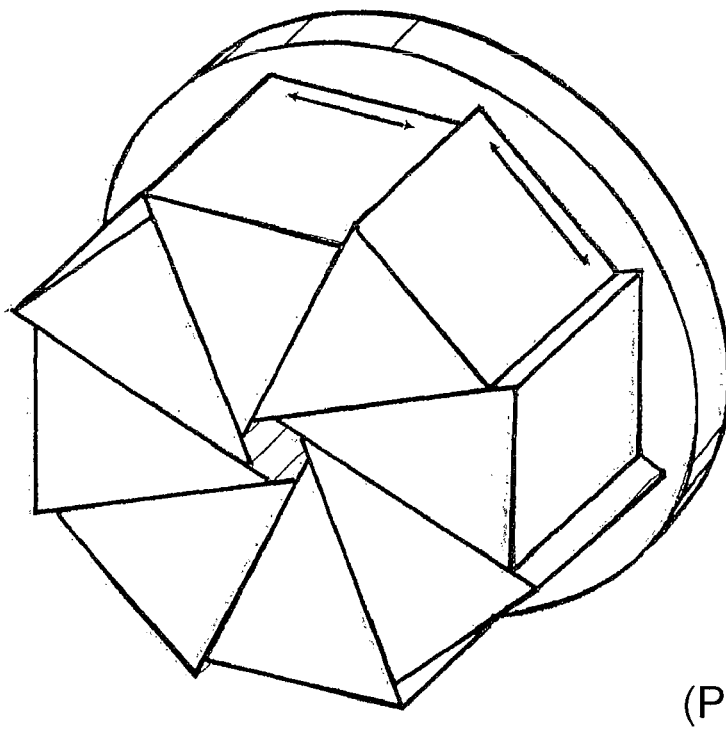
Figure 7:
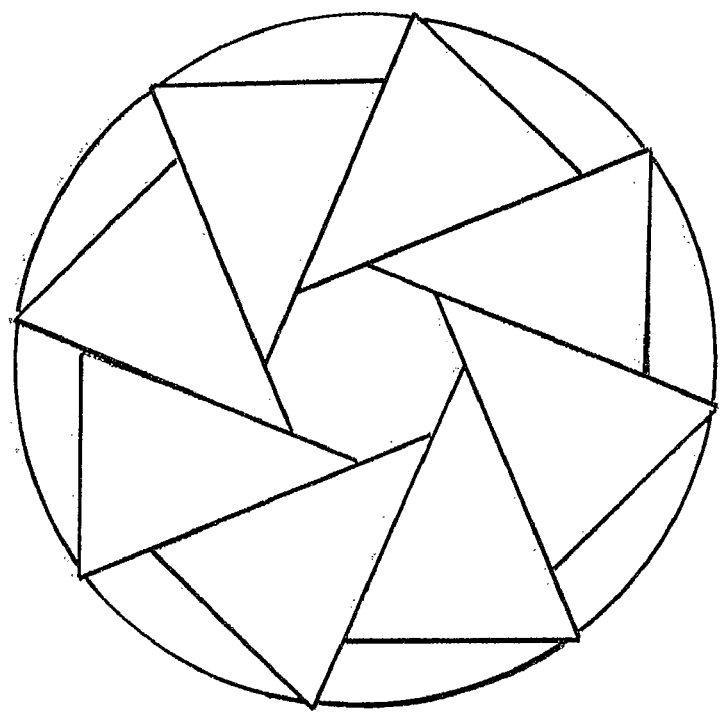
Figure 8:
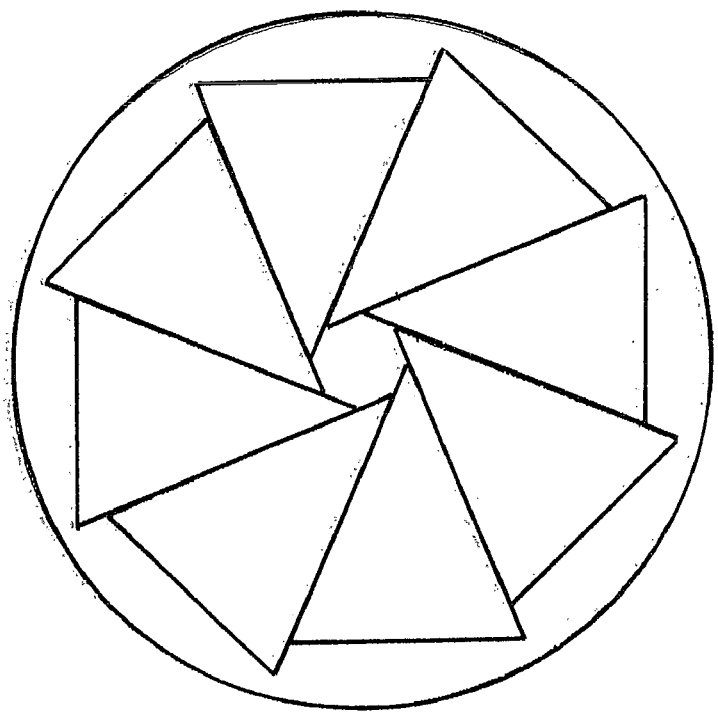
Figure 11:
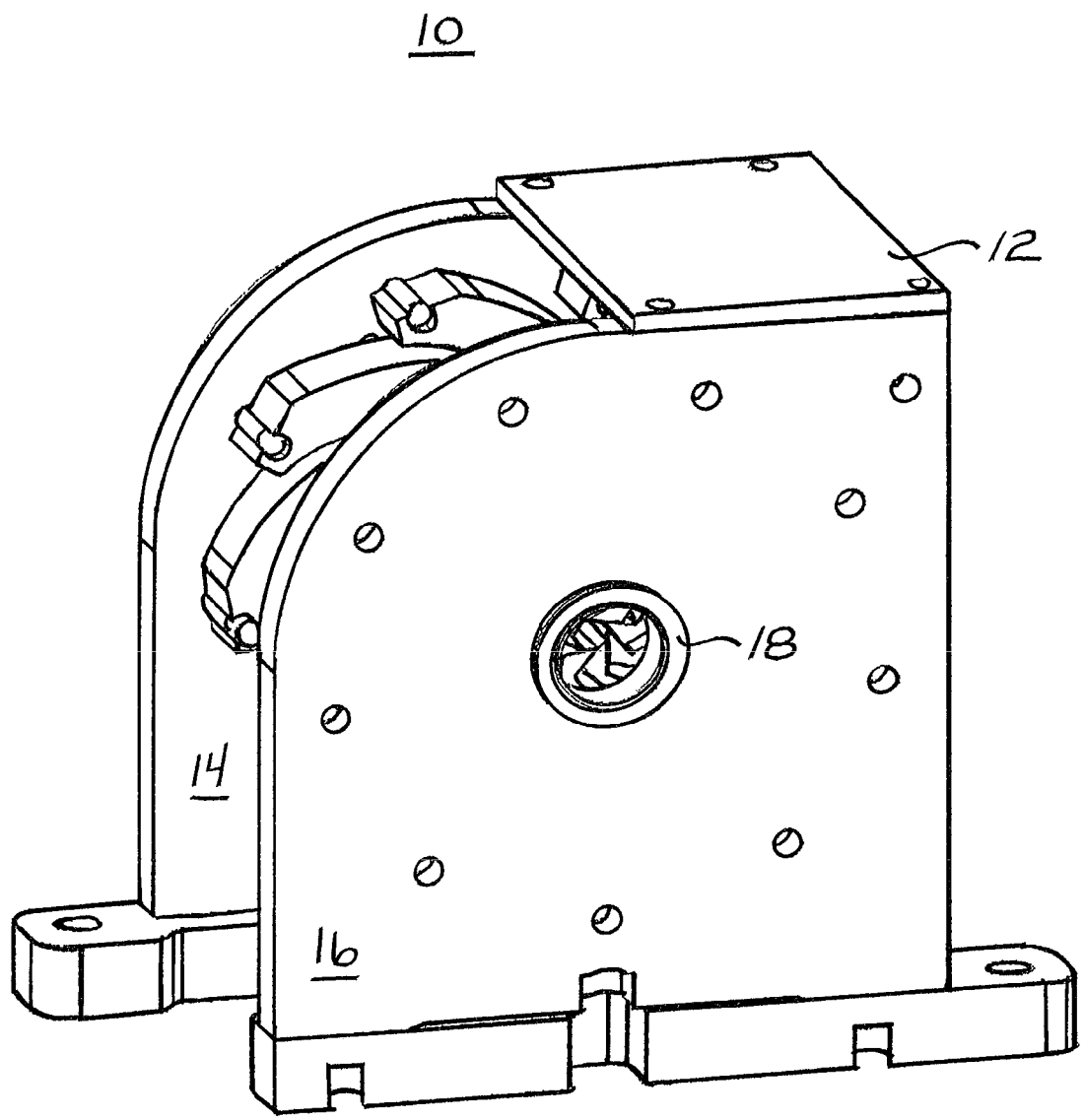
FIG. 11 is a receiving side view in perspective of a radial compression mechanism in accordance with the present invention.
Figure 13:
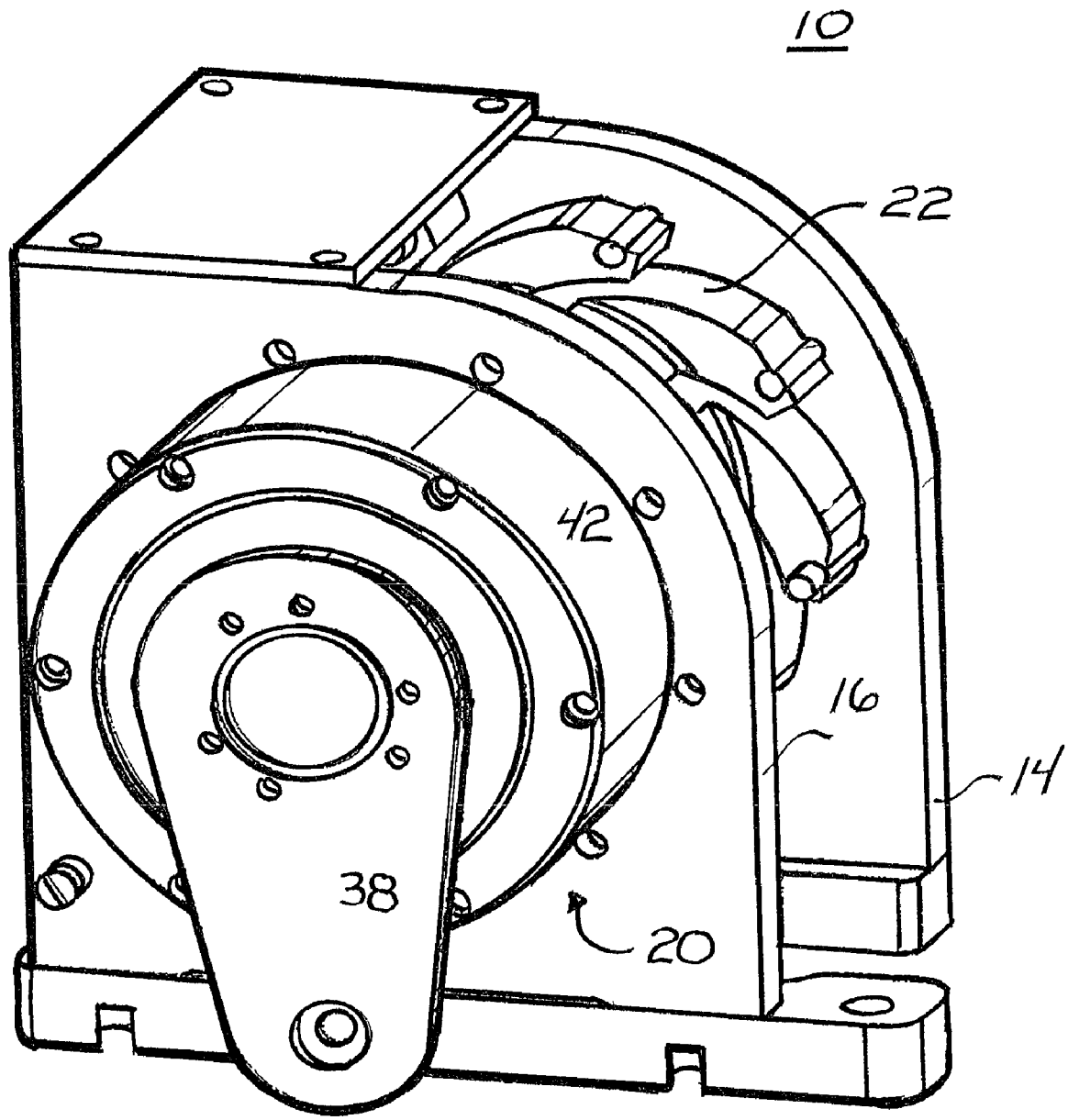
FIG. 13 is a crank side view in perspective of the radial compression mechanism of FIG. 1.

Turning now to the drawings, attention is first directed to FIGS. 11-17, which illustrate various perspective views of a radial compression mechanism 10 in accordance with the present invention. Mechanism 10 includes a housing 12 with a pair of spaced apart hinge plates 14 and 16. Hinge plate 16 has a product receiving opening 18 formed approximately centrally therethrough, an enlarged view of which can be seen in FIG. 12 Hinge plate 16 has a crank mechanism 20 mounted on the outer surface thereof that is coupled to rotatably drive a plurality of hinged or pivotally mounted die, designated 22. Each die 22 has a working surface 24 at an inner end and a pair of spaced apart pivot points 26 (seen for example in FIG. 15) at the other end. Each die 22 of the plurality of dies is mounted at one pivot point 26 by a pivot pin 28 engaged in hinge plate 14 and at the other pivot pin 26 by a pivot pin 28 engaged in hinge plate 16.

Referring specifically to FIG. 12, each die 22 is positioned in sliding engagement with a similar die 22 on adjacent sides so that working surfaces 24 of the plurality of die 22 cooperate to form an approximately cylindrical central cavity 30. Central cavity 30 has an axis that lies along the rotary axis of crank mechanism 20. As will be explained in more detail below, crank mechanism 20 can be operated to increase the diameter of central cavity 30 to a maximum and to decrease central cavity 30 continuously to a minimum. With central cavity 30 at a maximum, any device to be radially compressed, such as a stent, balloon, catheter, etc., is inserted through opening 18 into central cavity 30. Crank mechanism 20 is then operated to continuously reduce the diameter of central cavity 30 until the product is suitably compressed.

Figure 14:
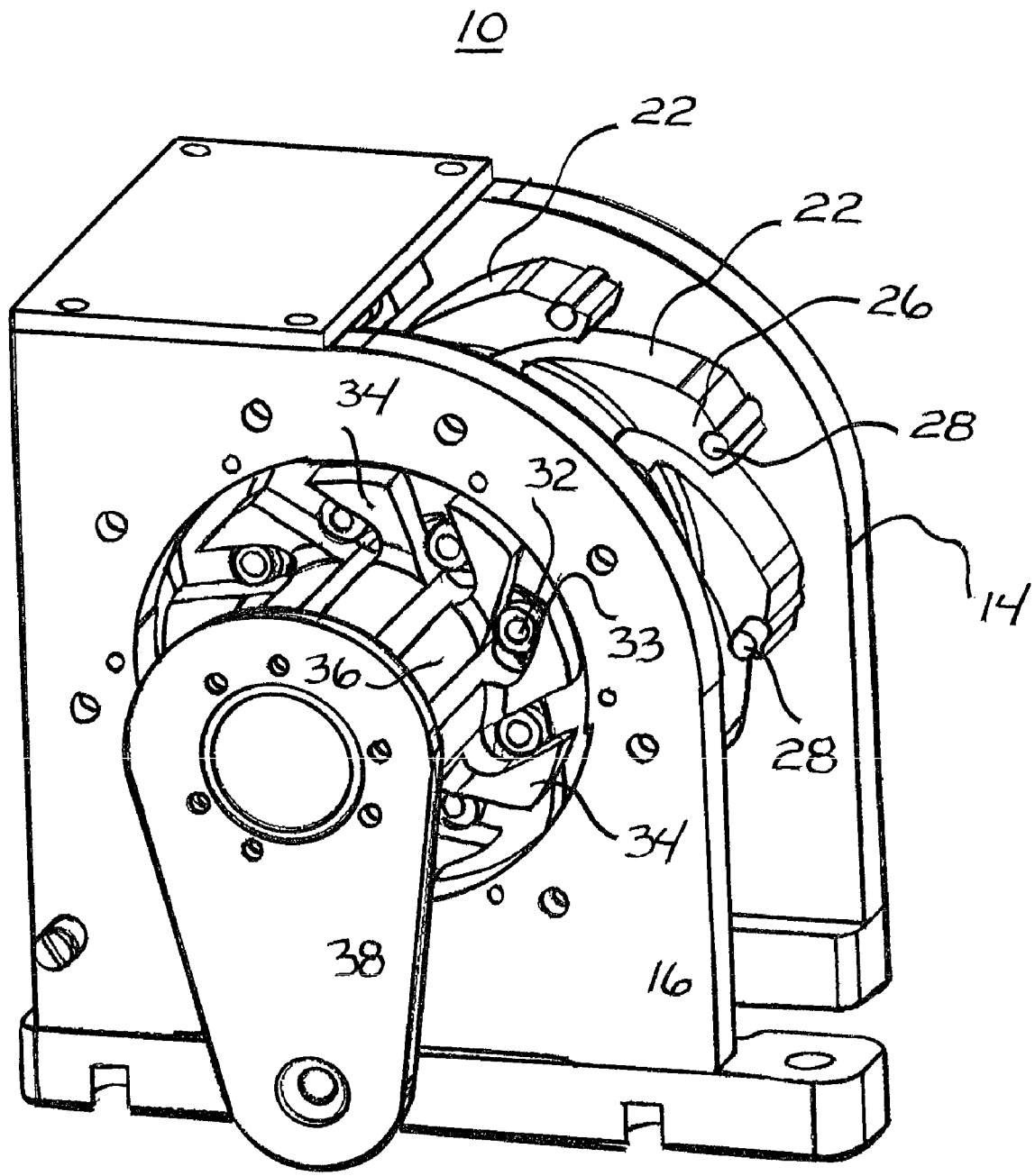
FIG. 14 is a view similar to FIG. 13, portions thereof removed to illustrate inner components.
Figure 15:
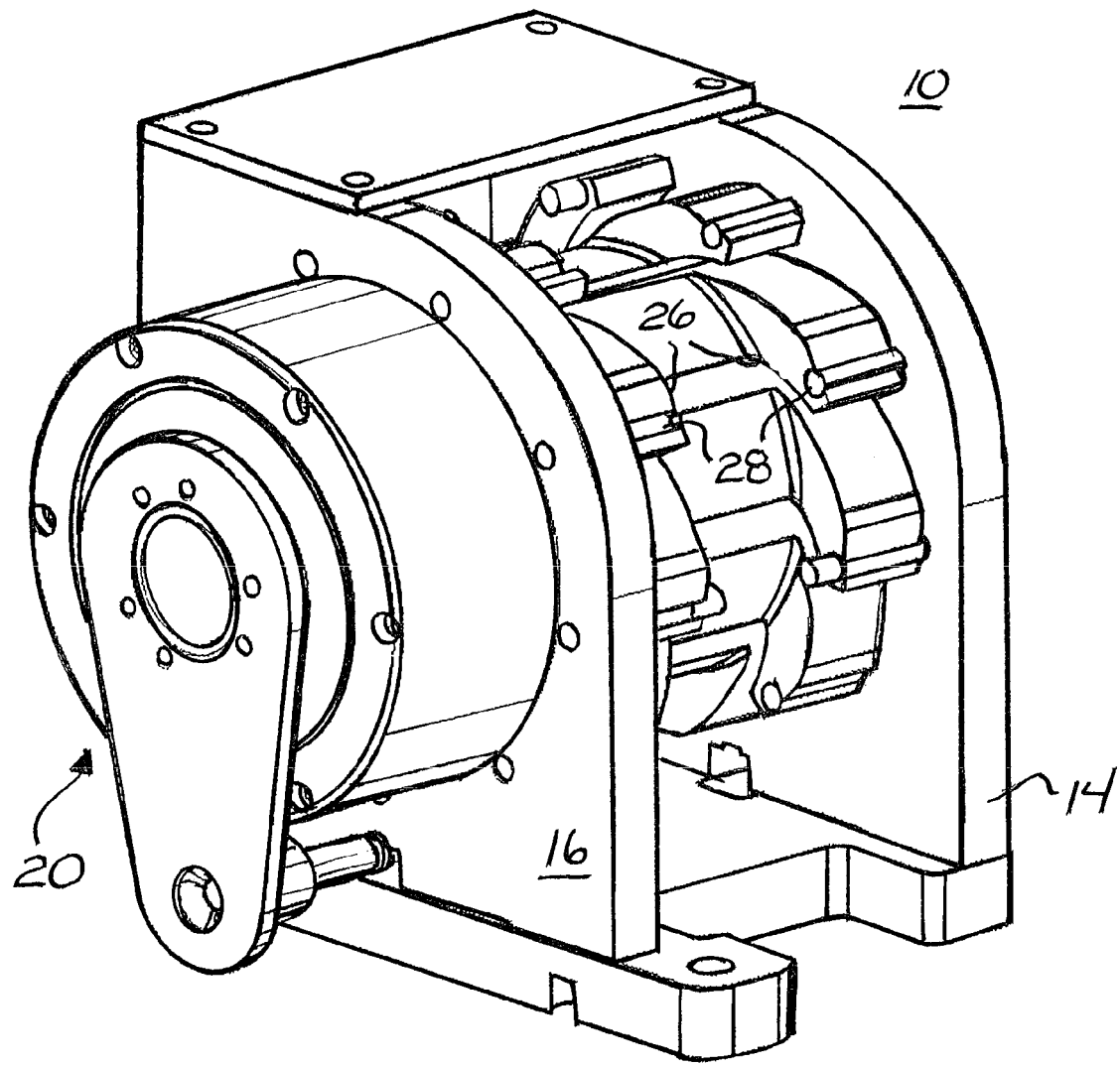
FIG. 15 is a front view in perspective of the radial compression mechanism of FIG. 1.
Figure 16:
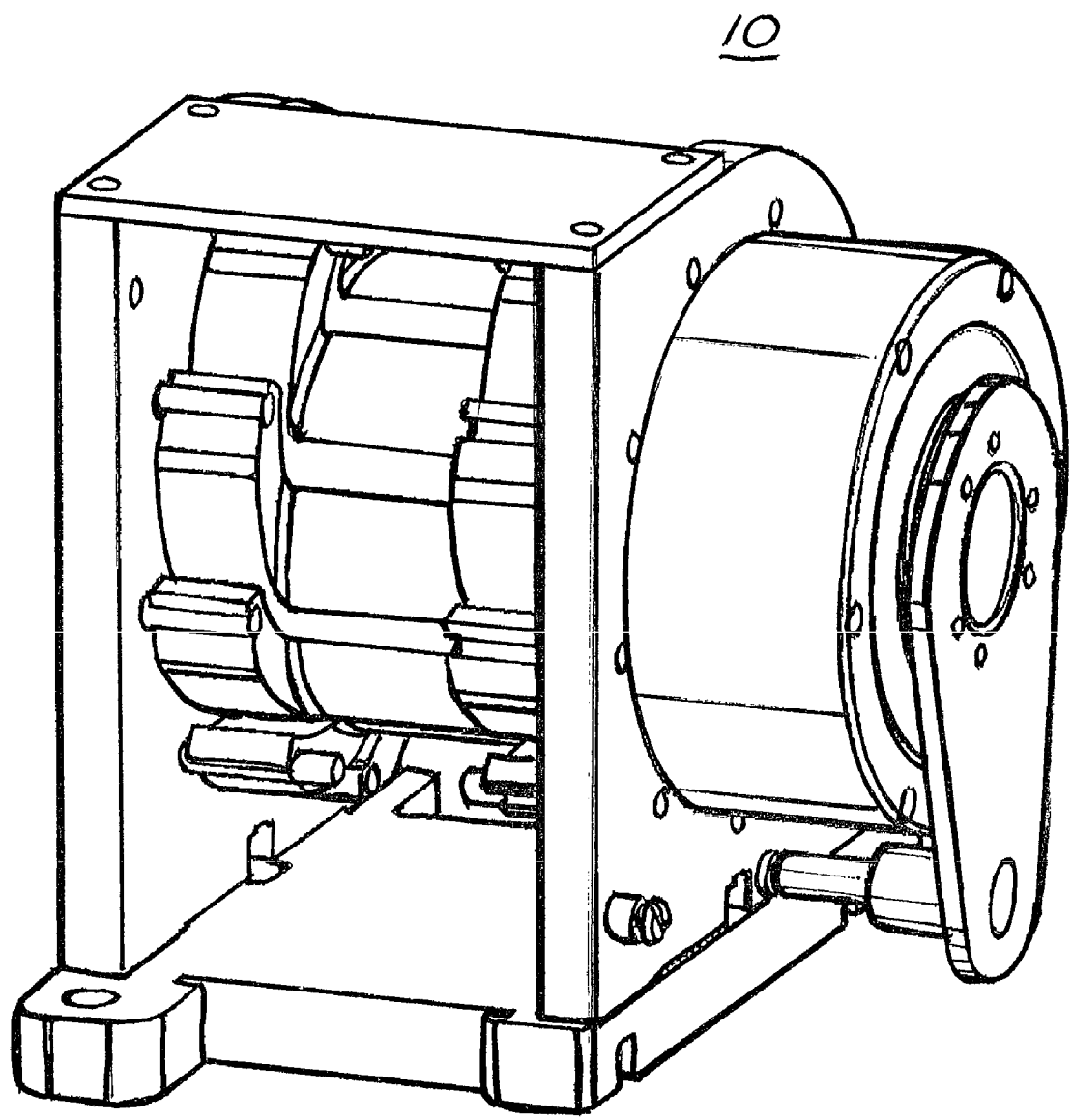
FIG. 16 is a rear view in perspective of the radial compression mechanism of FIG. 1.
Figure 17:
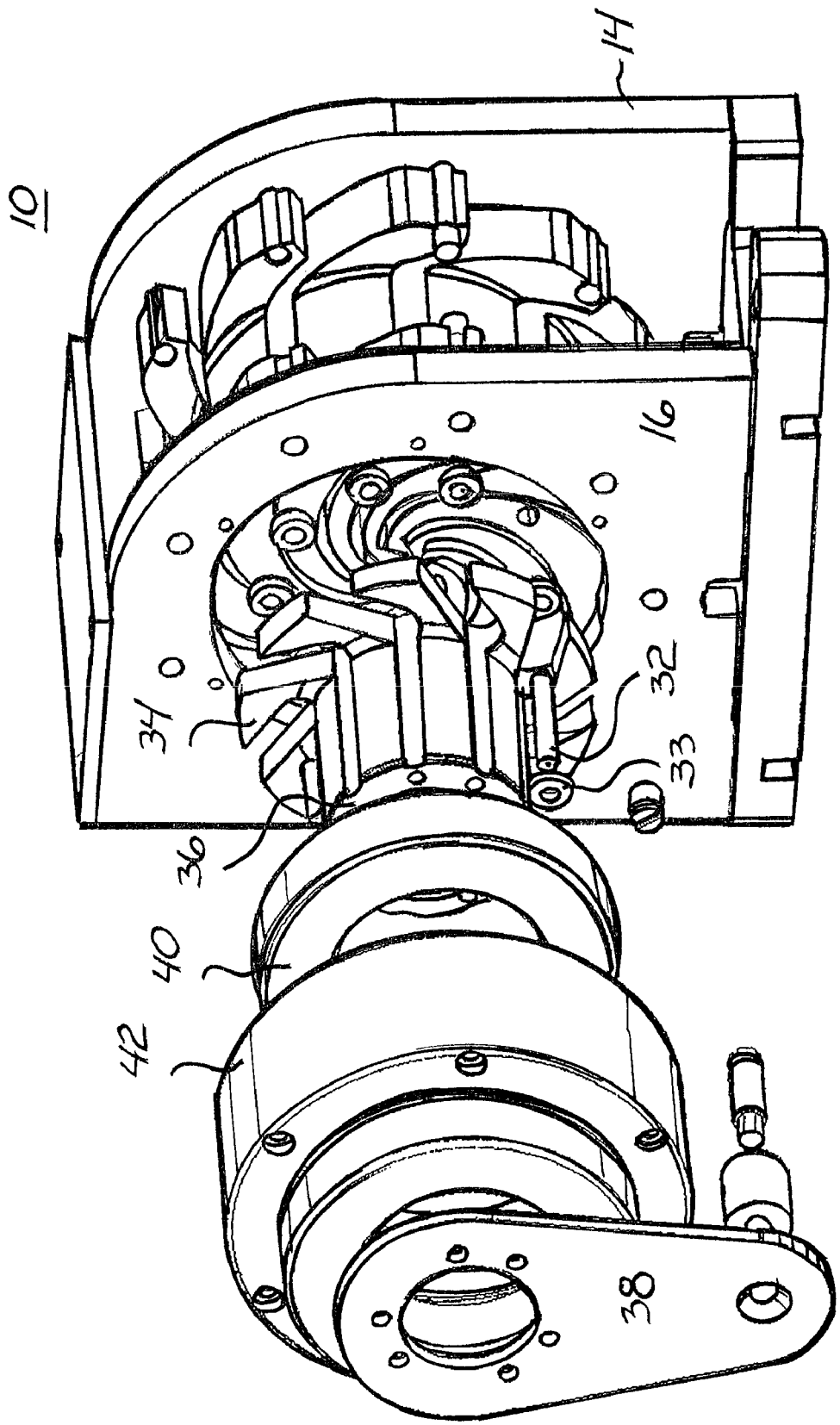
FIG. 17 is an exploded view in perspective of the radial compression mechanism of FIG. 1.
Figure 18:
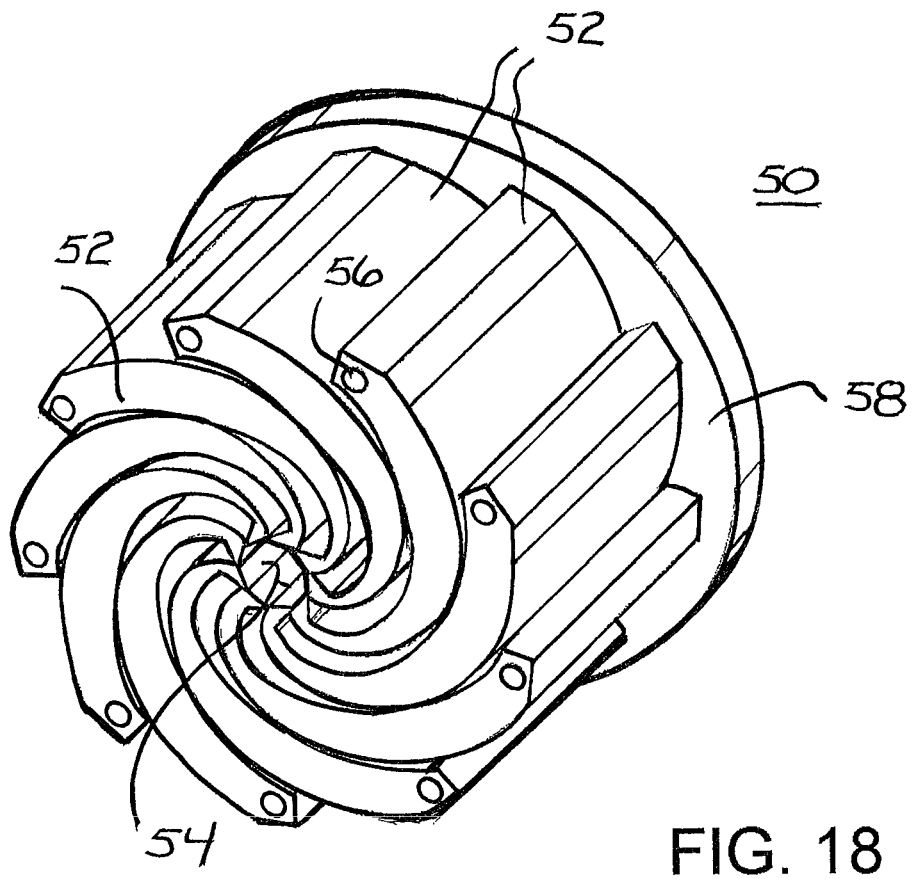
FIGS. 18-21 are sequential views illustrating the operation and shape of one embodiment of the die in the mechanism of FIG. 1.
Figure 19:
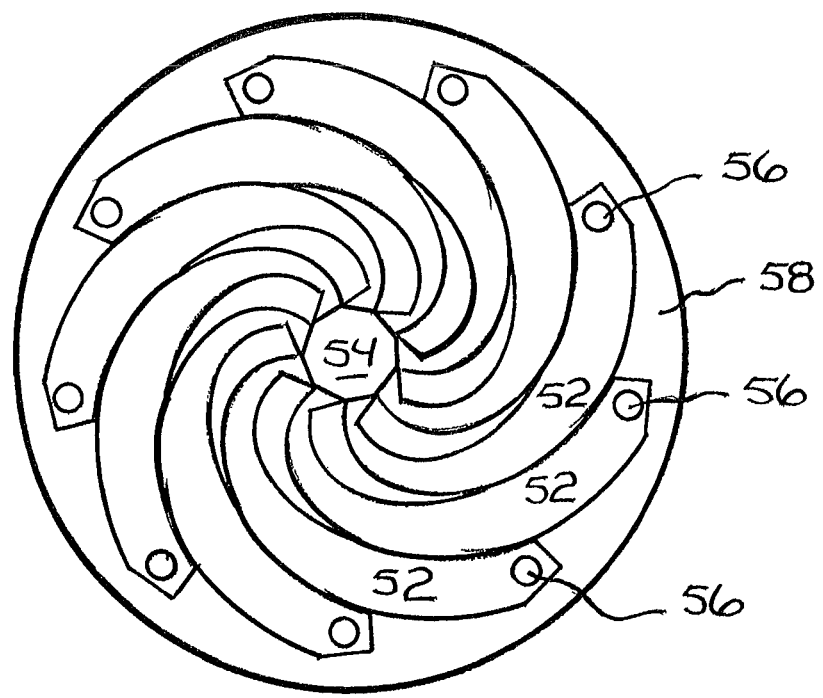

As best seen by referring to FIGS. 14 and 17, each die 22 has a drive pin 32 mounted thereon so as to extend outwardly toward hinge plate 16. A bearing 33 surrounds drive pin 32 and is engaged by one of several slots in a cam shaft 34 that is in turn attached to a crank arm 38. A ball bearing 40 is mounted within a bearing housing 42, attached to hinge plate 16, to mount cam shaft 34 for rotation about a central axis coaxial with the axis of central cavity 30. Each slot in the cam shaft 34 slideably or cammingly engages a bearing 33 and drive pin 32 to pivot the associated die 22, in conjunction with all of the other die, so as to open or close central cavity 30.

Here it should be noted that other means of driving the plurality of die to open or close central cavity 30 can be used but the drive should be configured to drive die 22 in unison so that movement of working surfaces 24 is uniform, i.e. to accurately impart the same rotational position or movement to all die 22. One example of an alternative mechanism is to position the drive pins on a rotating disk attached to, for example, a crank arm, and forming slots or camming surfaces on each die. The rotating drive pins then engage the camming surfaces and drive the die in unison to continuously and uniformly close or open the central cavity.

Turning now to FIGS. 18-21, one embodiment of a radial compression mechanism, designated 50, is illustrated. For purposes of this disclosure, the radial compression mechanism is considered to include the plurality of die and mounting mechanism. Because a great variety of driving mechanisms may be utilized they may or may not be included in the definition of the radial compression mechanism. Mechanism 50 includes a plurality of die, each die herein designated 52, pivotally mounted to define an approximately cylindrical central cavity 54 with a continuously changeable diameter. It will be understood that the plurality of die may vary over the practical range of 5 to 15, depending upon the application and desires of the manufacturer. Each die 52 is pivotally mounted by means of a pivot pin 56, adjacent an outer end, to a hinge plate 58. Each die 52 has a generally arcuately shaped body ending at an inner end opposite the outer end. Further, the inner end is formed with a working surface 60 and a sliding surface 62 which join at a tip to form an included angle less than 45 degrees.

Figure 20:
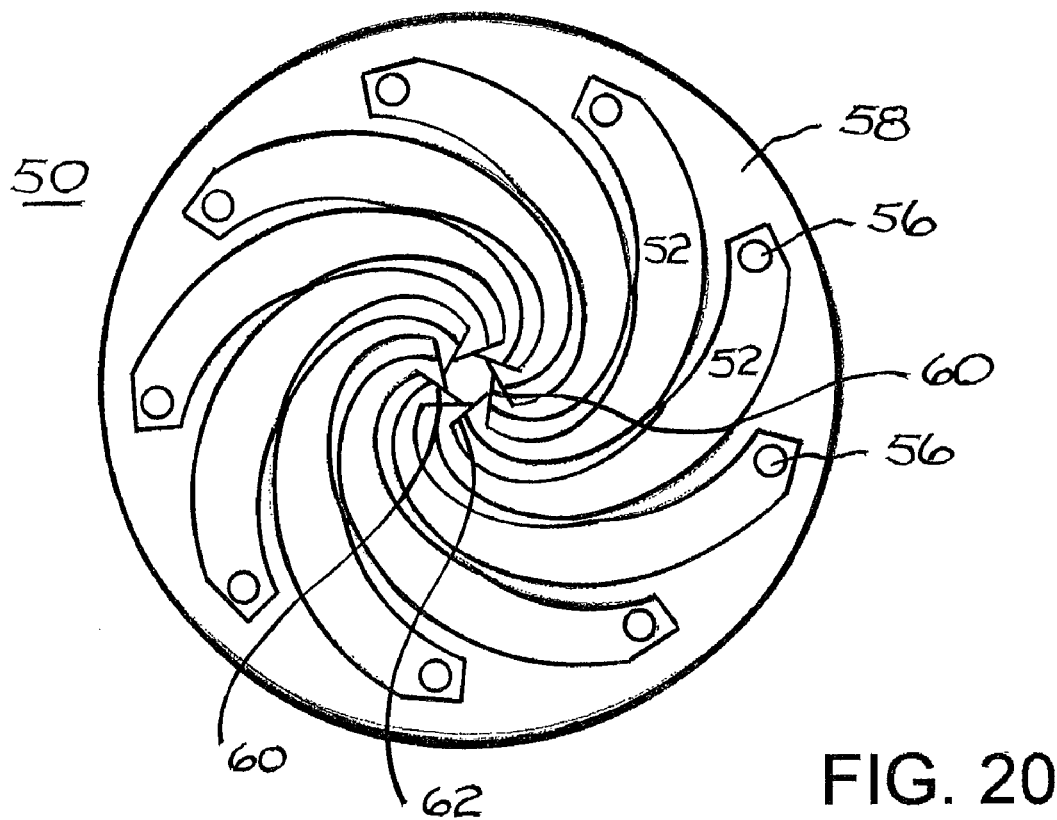
Figure 21:
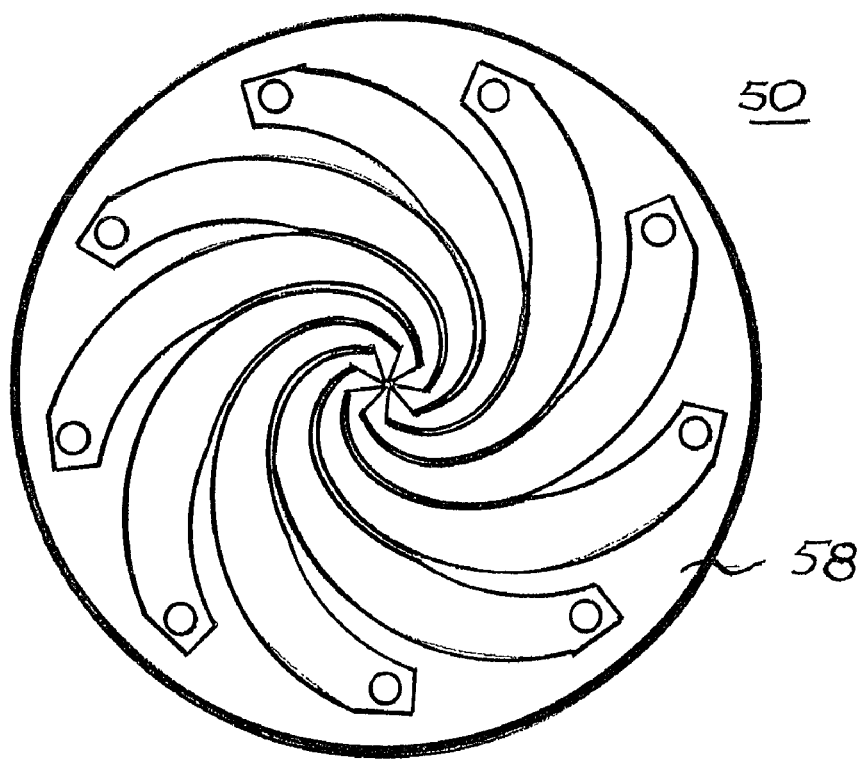

In operation, as all of die 52 are rotated in unison, sliding surface 62 of each die 52 "slideably engages" the working surface 60 of the adjacent die 52 and the exposed portion of working surfaces 60 cooperate to define central cavity 54. As explained in more detail below, sliding surfaces 62 may not actually touch working surfaces 60 but the term "slideably engages" is used herein to more visually explain the movement. When sliding surfaces 62 are adjacent the edge of working surface 60 farthest from the tip, central cavity 54 is at a maximum (see FIG. 19). As all of die 52 are rotated in unison, sliding surface 62 gradually covers more of working surface 60 and the diameter of central cavity 54 becomes smaller, as depicted in FIG. 20, until sliding surface 62 substantially covers working surface 60 and central cavity 54 is at a minimum, as depicted in FIG. 21.

Figure 22:
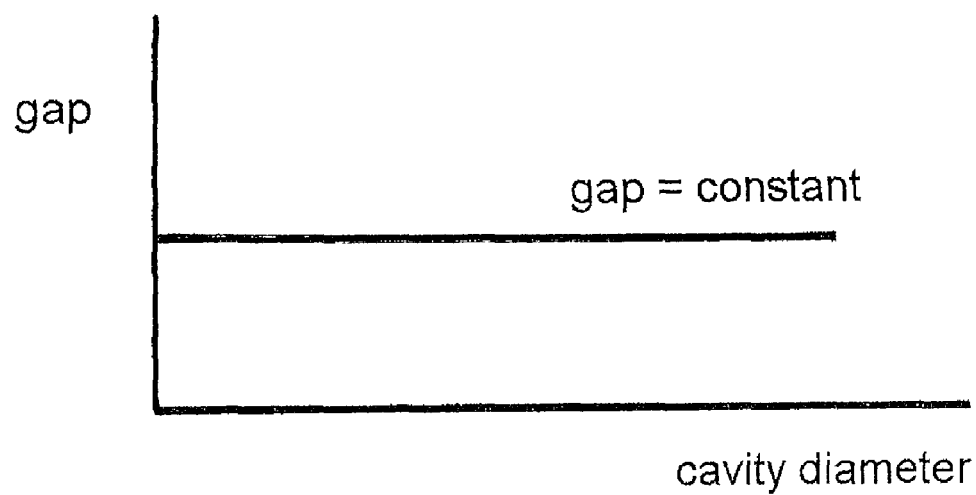
FIG. 22 illustrates graphically the relationship between the diameter of the central opening and die-to-die gaps for the embodiment of FIG. 18.
Figure 23:
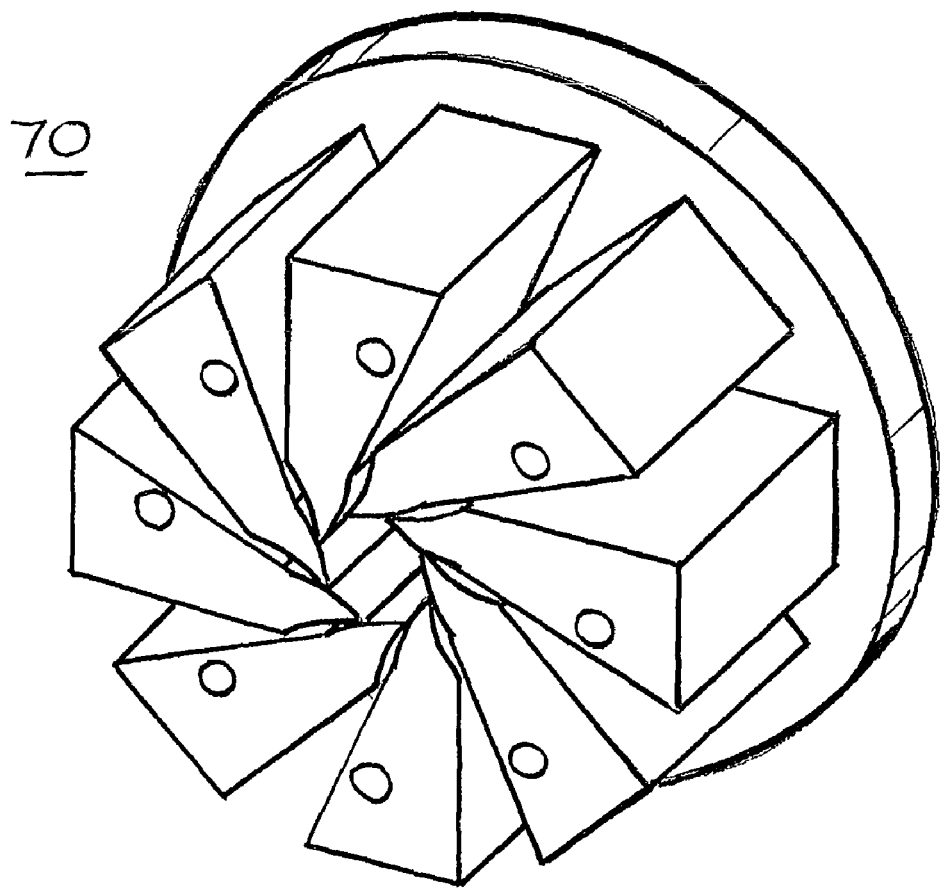
FIGS. 23-26 are sequential views illustrating the operation and shape of another embodiment of the die in the mechanism of FIG. 1.
Figure 24:
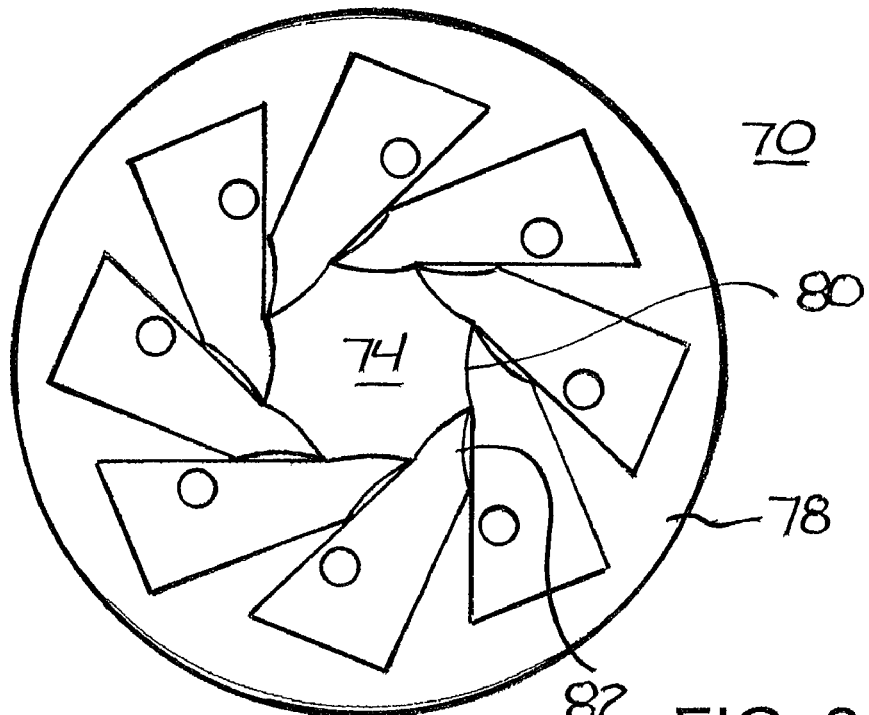

Here it should be noted that working surfaces 60 and sliding surfaces 62 may not actually be in sliding engagement but may (and preferably will) be held with a slight gap therebetween by the mounting and driving mechanism. By not actually being in sliding engagement, frictional wear can be substantially reduced and the possibility of minute metal scrapings in the product can be eliminated. Generally, the working surfaces 60 are not planar, but have a specifically-designed shape that makes the gap between adjacent die 52 an arbitrary function of the diameter of central cavity 54, which function can be chosen by the designer. Typically, the gap will be chosen to be approximately constant (see FIG. 22), independent of the diameter, and as small as manufacturing tolerances will allow. To design the shape of the working surface to achieve a constant gap, the designer choses a distance from the hinge point to the die tip, then rotates the die so that the tip moves in an arc about the hinge point. Knowing that the working surface of the adjacent die must remain a small distance from the tip as both die rotate in unison, the designer can perform a kinematic analysis to define the shape of the working surface. The analysis may be done using, for example, algebraic equations which are solved using software such as Mathcad. Or an approximate kinematic analysis can be done by assuming a circular-arc shape of the working surface, then choosing the center position and the radius of the arc by trial-and-error with the aid of solid-modeling software such as Solidworks. In the embodiment illustrated in FIGS. 18-21, pivot pin 56 of each die 52 is located approximately on the opposite side of mechanism 50 from the working tip of the die.

Turning now to FIGS. 23-26, another embodiment of a radial compression mechanism 70 in accordance with the present invention is illustrated. Mechanism 70 includes a plurality of die, each die herein designated 72, pivotally mounted to define an approximately cylindrical central cavity 74 with a continuously changeable diameter. It will be understood that the plurality of die may vary over the practical range of 5 to 15, depending upon the application and desires of the manufacturer. Each die 72 is pivotally mounted by means of a pivot pin 76, adjacent an outer end, to a hinge plate 78. Each die 72 has a generally triangularly-shaped body ending at an inner end opposite the outer end. Further, the inner end is formed with a generally arcuately-shaped (convex) working surface 80 and a generally arcuately-shaped (concave) sliding surface 82 which join at a tip to form an included angle less than 45 degrees. The working surface is generally convex, but the slide surface can be any shape. The reason the sliding surface is shown as concave is that the shape allows the die to have the most material, to be as strong and stiff as possible. The same is true about the sliding surface of the arcuate dies of the previous embodiment.

Figure 25:
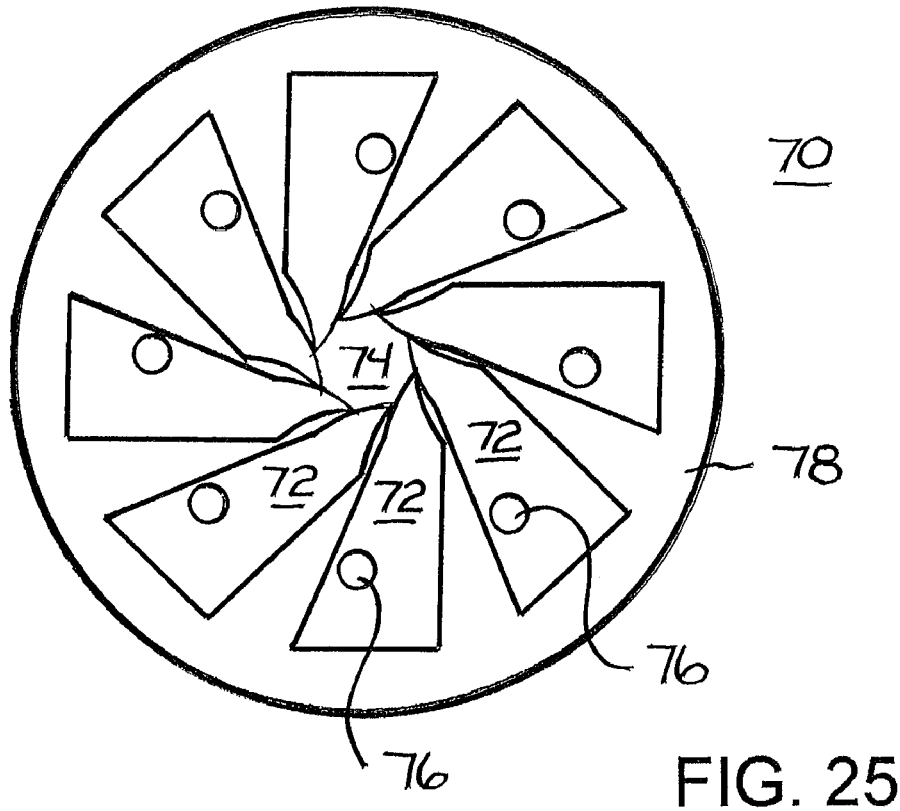
Figure 26:
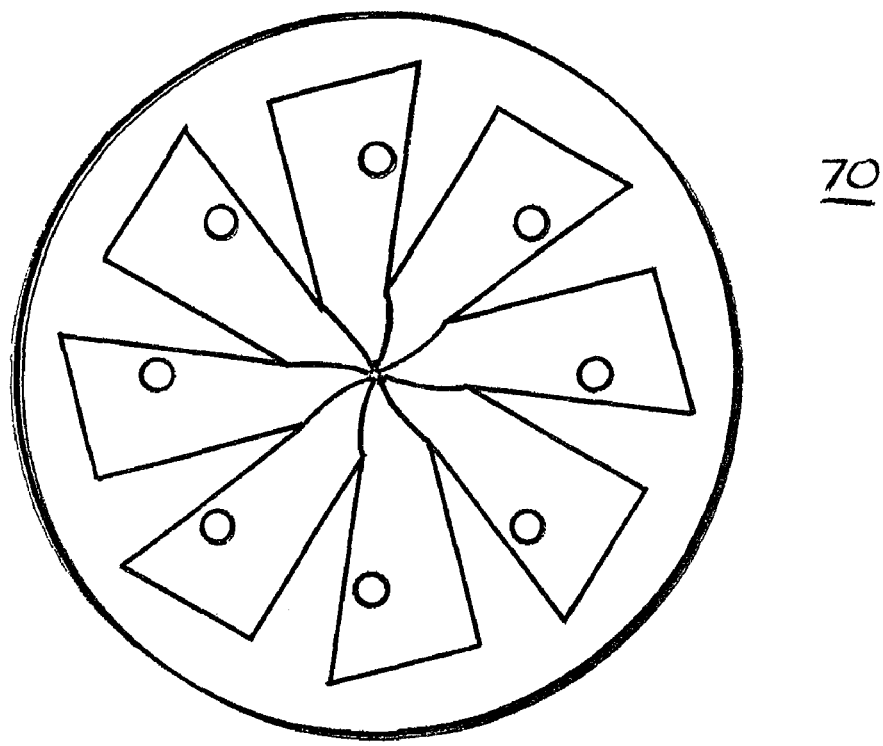

In operation, as all of die 72 are rotated in unison, sliding surface 82 of each die 72 "slideably engages" the working surface 80 of the adjacent die 72 and the exposed portion of working surfaces 80 cooperate to define central cavity 74. As explained in more detail below, sliding surfaces 82 may not actually touch working surfaces 80 but the term "slideably engages" is used herein to more visually explain the movement. When sliding surfaces 82 are adjacent the edge of working surface 80 farthest from the tip, central cavity 74 is at a maximum (see FIG. 24). As all of die 72 are rotated in unison, sliding surface 82 gradually covers more of working surface 80 and the diameter of central cavity 74 becomes smaller, as depicted in FIG. 25, until sliding surface 82 substantially covers working surface 80 and central cavity 74 is at a minimum, as depicted in FIG. 26.

Figure 27:
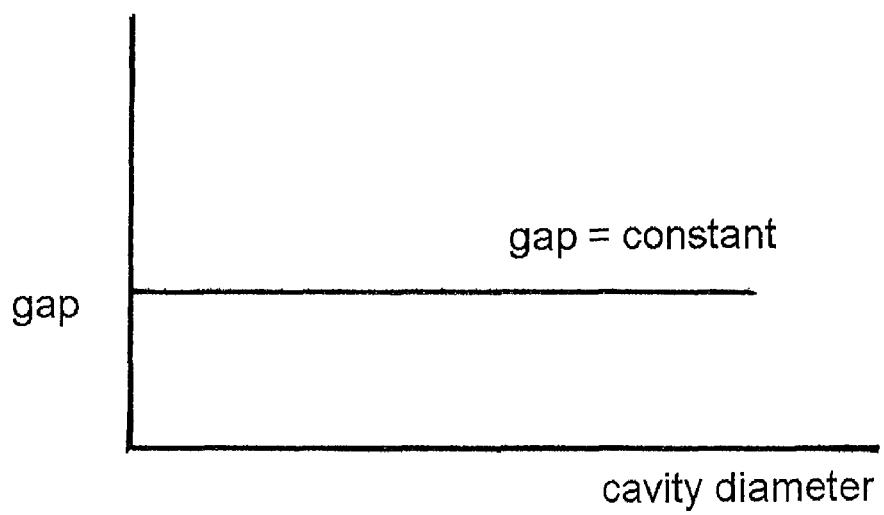
FIG. 27 illustrates graphically the relationship between the diameter of the central opening and die-to-die gaps for the embodiment of FIG. 23.

Here it should be noted that working surfaces 80 and sliding surfaces 82 may not actually be in sliding engagement but may (and preferably will) be held with a slight gap therebetween by the mounting and driving mechanism. Generally, the working surfaces 80 and sliding surfaces 82 are arcuate and with a specifically-designed shape that makes the gap between adjacent die 72 an arbitrary function of the diameter of central cavity 74, which function can be chosen by the designer. Typically, the gap will be chosen to be approximately constant (see FIG. 27), independent of the diameter, and as small as manufacturing tolerances will allow.

A slight disadvantage of mechanism 70, the embodiment illustrated in FIGS. 23-26, is that when designed to provide a substantially constant gap between adjacent die 72, working surfaces 80 that form central cavity 74 are slightly convex, decreasing the roundness of central cavity 74. Mechanism 50, illustrated in FIGS, 18-21, is a preferred embodiment. One of the reasons being that working surfaces 60, when designed to provide a substantially constant gap between adjacent die 52, are slightly concave, making central cavity 54 more round.

Thus, a new and novel radial compression mechanism has been disclosed. The new and novel radial compression mechanism is constructed to operate with a constant gap between adjacent die and to move the die in unison between a maximum diameter central cavity and a minimum diameter central cavity with a continuous radial movement. Therefore, the changing and relatively large gap of some prior art devices or the extremely difficult linear movement of other prior art devices has been overcome.

Various changes and modifications to the embodiment herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. Radial compression mechanism comprising:
   a plurality of dies each including a generally wedge-shaped body having an outer end pivotally attached to a hinge plate and an inner working tip, the plurality of dies being mounted on the hinge plate in an inwardly directed orientation with the outer ends being positioned in a circle and the working tips cooperating to define a central product-receiving cylindrically-shaped cavity having a transitional diameter coaxial with the circle, the product-receiving cavity being transitional between an open and a closed orientation;

each die of the plurality of dies having a sliding surface and a working surface with a juncture of the sliding surface and the working surface defining the working tip, the working surface of each die of the plurality of dies being substantially convex, the sliding surface of each die being positioned in juxtaposition to the working surface of an adjacent die and a constant width gap being defined between the working tip of each die of the plurality of dies and the working surface of the adjacent die of the plurality of dies; and driving mechanism coupled to each die of the plurality of dies to rotatably drive all of the die of the plurality of dies in unison to transition between the open and closed orientations, the width of the gap remaining constant in the open and closed orientations and during the transition between the open and closed orientations.

2. Radial compression mechanism as claimed in claim 1 wherein the width of the gap is independent of the diameter of the product-receiving cavity.

3. Radial compression mechanism as claimed in claim 1 wherein the width of the gap is less than 0.3 mm wide.

* * * * *